(12) United States Patent
Schmidt et al.

(10) Patent No.: US 8,175,674 B2
(45) Date of Patent: May 8, 2012

(54) BELT DEVICE

(75) Inventors: Ralf Schmidt, Aachen (DE); Jens Muehlsteff, Aachen (DE); Kirsten English, Cologne (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1236 days.

(21) Appl. No.: 11/911,824

(22) PCT Filed: Apr. 4, 2006

(86) PCT No.: PCT/IB2006/051022
§ 371 (c)(1),
(2), (4) Date: Oct. 18, 2007

(87) PCT Pub. No.: WO2006/111875
PCT Pub. Date: Oct. 26, 2006

(65) Prior Publication Data
US 2008/0200792 A1    Aug. 21, 2008

(30) Foreign Application Priority Data

Apr. 19, 2005   (EP) .................................... 05103131

(51) Int. Cl.
*A61B 5/0408* (2006.01)
(52) U.S. Cl. ........................................ 600/390; 600/393
(58) Field of Classification Search .................. 600/386, 600/388, 390, 393
See application file for complete search history.

(56) References Cited

U.S. PATENT DOCUMENTS

| 4,498,480 | A |   | 2/1985 | Mortensen |
|---|---|---|---|---|
| 4,709,704 | A | * | 12/1987 | Lukasiewicz ................. 600/382 |
| 4,854,323 | A |   | 8/1989 | Rubin |
| 5,445,149 | A | * | 8/1995 | Rotolo et al. ................. 600/382 |
| 6,115,623 | A |   | 9/2000 | McFee |
| 6,119,516 | A | * | 9/2000 | Hock ............................. 600/547 |
| 6,400,975 | B1 | * | 6/2002 | McFee .......................... 600/372 |
| 6,408,200 | B1 | * | 6/2002 | Takashina ..................... 600/382 |
| 6,551,252 | B2 | * | 4/2003 | Sackner et al. ............... 600/536 |
| 6,584,343 | B1 |   | 6/2003 | Ransbury et al. |
| 2003/0158593 | A1 |   | 8/2003 | Heilman et al. |
| 2008/0154110 | A1 | * | 6/2008 | Burnes et al. ................. 600/382 |
| 2008/0287770 | A1 | * | 11/2008 | Kurzweil et al. ............. 600/388 |

FOREIGN PATENT DOCUMENTS

| EP | 1095612 A1 | 5/2001 |
|---|---|---|
| WO | 0160250 A1 | 8/2001 |

* cited by examiner

*Primary Examiner* — Lee Cohen

(57) ABSTRACT

The belt device comprises a torso portion, a collar portion, sensor elements and at least a first and a second closure element. The first closure element is part of the collar portion on the front side and a second closure element is part of the torso portion on the front side. The closure elements arranged in such a way that they can be opened by a wearer in a comfortable way. The user is able to put on and off the belt system without help of a third person. By the ability to combine different sized collar portions with different sized torso portions a belt device system is provided.

15 Claims, 3 Drawing Sheets

BELT DEVICE

The invention is directed on a belt device. The system is especially usable for wearing ECG electrodes.

A portable ECG apparatus and method is described in EP 1 095 612 A1. The portable ECG apparatus comprises an electrode garment and a diagnostic system. The electrode garment is a vest having a plurality of electrodes attached at strategic locations. The electrode-garment can include means for manually placing each of the electrodes on a variety of customized positions and such positions can be marked, so that the electrodes can be changed. Then one coded garment can be shared by a number of individuals. It is contemplated that the electrode-garment can have a means to automatically control placement of each electrode, such as through use of a pair of motors, which move each electrode in plane. Further the vest consists of a torso portion and a pair of shoulder straps. The torso portion is preferably made of a material that is comfortable on the skin, such as nylon fabric. The torso portion is closable by Velcro. The electrode garment is connected to the diagnostic system, wherein the diagnostic system presents diagnoses, which are understandable to a layperson.

The company Leidel & Kracht GmbH, Bremerhavenerstrasse 39, D-50735 Köln distributes to possible customers samples for advertising the professional skills of the company. These samples show a foamed material piece, comprising integrated slots, wherein a scale is arranged parallel to the slot. The bottom of the slots are covered with Velcro. The Velcro could be used as a part of a fastener.

It is an object of the invention to provide a belt device that can be easily put on by the wearer on his/her own. It is further object of the invention to provide a belt device system, which could be adapted to a wearer in a comfortable way.

The problem of the invention is solved by the use of a belt device comprising a torso portion, a collar portion, sensor elements and at least a first and a second closure element, wherein the first closure element is part of the collar portion and arranged on the front side of the belt device. So it is easy for the wearer to open and to close the first closure element. A second closure element is part of the torso portion and is arranged on the front side also, wherein opening and closing of both closure elements could be handled by the wearer in a comfortable way.

In one embodiment the collar portion is detachably connected to the torso portion by at least one adjustable connection element. By the use of the adjustable connection element the collar portion could be adjusted to the height of the upper part of the wearers body.

In one embodiment at least two connection elements are arranged, wherein the collar portion is connectable and disconnectable to a torso portion. By choosing a range, wherein an adjustment is possible, the needed number of collar portions to cover a range of different sized people is determined. In one embodiment one of the front closure elements enables to connect the collar portion with the torso portion.

A belt device system is provided by a number of collar portions of different size, which are connectable to torso portions of different size. By choosing one of the collar portions and one of the torso portions and connecting of them a belt device is supplied. To reduce the number of needed collar portions a range is chosen between 5 and 25 cm. The collar portion will be well fitted to the body of the wearer to guarantee a good sensor skin contact. A good skin sensor contact is needed for generating reliable sensor signals.

In one possible embodiment the adjustable connection is arranged at the backside of the belt device. By the arrangement of the adjustable connection on the backside an unwanted readjustment by the wearer is avoided.

By the possibility of an adjustment the belt system is usable for different sized people.

Especially for ECG measurement it is very important that the sensors are in good skin contact. By the use of a soft and flexible material, wherein sensors are kept by that parts, the soft parts will snuggle against the skin, which have a positive effect on the sensor to skin contact. Further it is more comfortable to wear the belt device.

In one possible embodiment the belt device comprises one or more pressure elements, which are assigned to the sensors. By a pressure element a continuously contact of the sensor to the skin of the wearer is improved. Especially adjustable pressure elements could be used, for example gel pads. Therefore the pressure could be adjusted to guarantee a pre-given contact pressure of the sensor to the skin of the wearer independent of the bumpiness of the skin surface. Very often elderly or obesity people have a very bumpy skin surface, wherein these people belong to the risk group of heart diseases. By measuring the ECG over long periods or more often the risk to die of heart diseases will be reduced.

In one possible embodiment at least one of the closure elements comprises an electric connection for power and/or data transfer.

In one of the possible embodiments an adjustable torso portion is used. The length of the torso portion can be adjusted in pre-given range. By choosing a range of adjustability the number of needed torso portion is determined to be able to fit one of available torso portions to any patient or wearer. By choosing a small range of adjustability the number of needed torso portion is going up. By using a large range of adjustability it is less comfortable for the wearer.

In one possible embodiment a range of adjustability between 5 cm to 25 cm is chosen, especially steps around 20 cm results in a manageable amount of different sized torso portions.

In a possible embodiment the sensor elements held by the belt device in such a way that the positions of the sensor are adjustable. The sensor position can be changed in respect to the torso or collar portion. Especially a possibility to shift the sensor element in a range of 2-7 cm is useful. Different sensor position could be linked with different ranges of adjustability.

A belt device system is build up by a number of collar portions of different size and a number of torso portion of different size, wherein all collar portions are connectable with all torso portions of the system. In dependence of the chosen adjustability of the collar portion and the torso portions the number of different sized torso and collar portions are determined to cover a pre-given range of different sized people. By a combination of a selected collar portion and a selected torso portion a suitable belt device for different sized people is provided.

Figure 1:
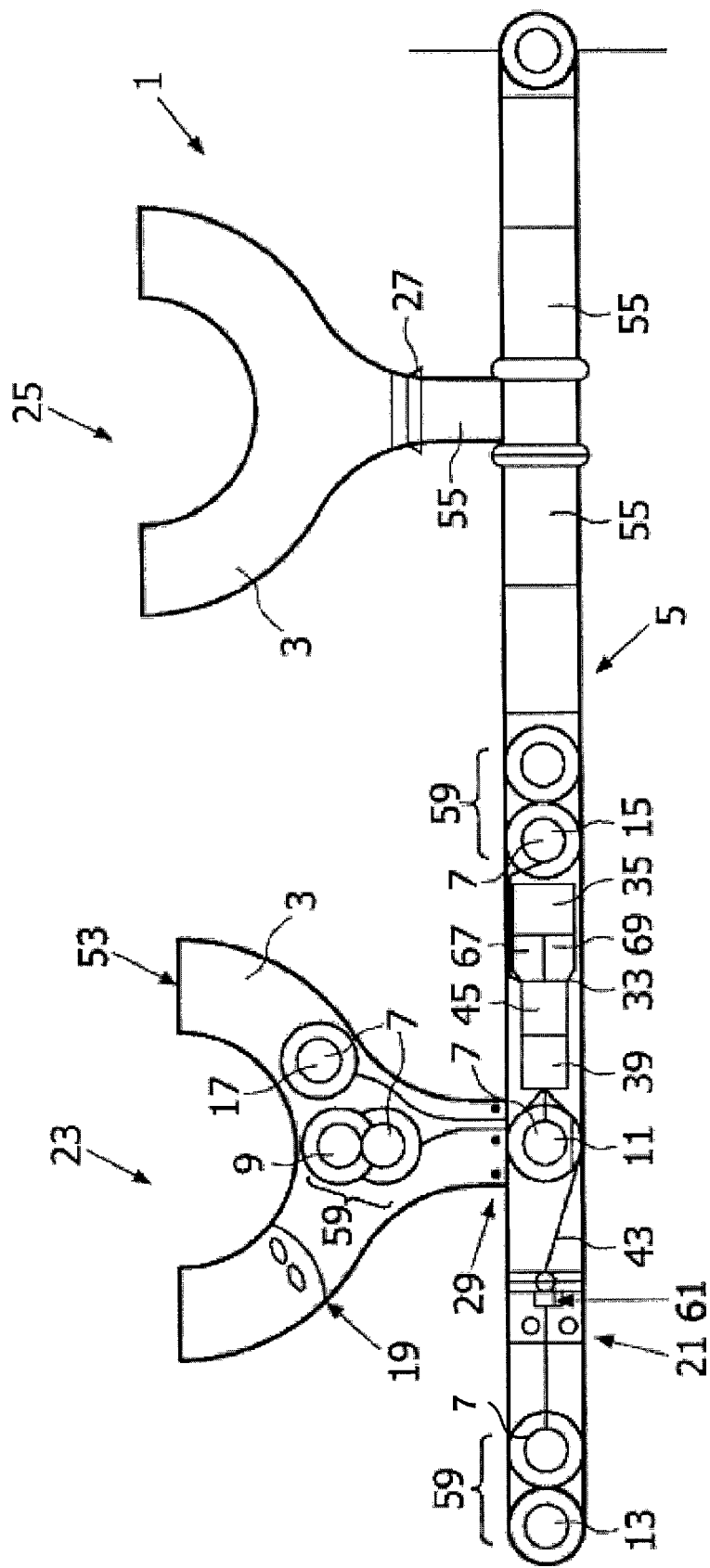
FIG. 1 shows a belt device.

In FIG. 1 a belt device is shown. The electrodes are held by this belt device. The number of the used electrodes and electrode positions is dependent on the used algorithm to generate results. In the shown example the sensor signals are used to generate an electrocardiogram (ECG).

The standard of a diagnostic clinical electrocardiogram (ECG) is a 12-lead (channel) ECG deduced from the readings of 10 electrodes placed at specific positions at the chest. Usually, trained professionals places glued electrodes at the required anatomical positions. Zymed Medical Instrumentation, now part of Philips Medical Systems, introduced a reduced electrode configuration for 12-lead ECG, which is named EASI LEAD and described in WO0160250, which is hereby incorporated by reference. By using EASI LEAD, five electrodes, placed at specific anatomic landmarks, provide 3 channels that contain sufficient information to calculate the 12 lead ECG.

The measurement of a 12-lead ECG both with a conventional and the EASI lead electrode configuration needs accurate electrode placement that is not feasible for a layman. A wearable belt device for electrodes and electronics that enables an easy and repeatable placement of the electrodes on the chest (EASI leads) by a layperson is proposed. The electrode positions within the belt device are adjustable to fit the individual anatomy. That adjustment should be done by a professional once and is not to be changed by the wearer. To put the wearable belt device on, the belt device can be opened without touching the electrode positions. Electrodes, cables and electronics are fastened to the belt device. Preferably the belt device comprises cable ducts that allow separate production of the electronic parts and the belt device, easy assembly and easy separation, e.g. for cleaning. It is also possible to integrate the cable inside of the body of belt device.

Figure 2:
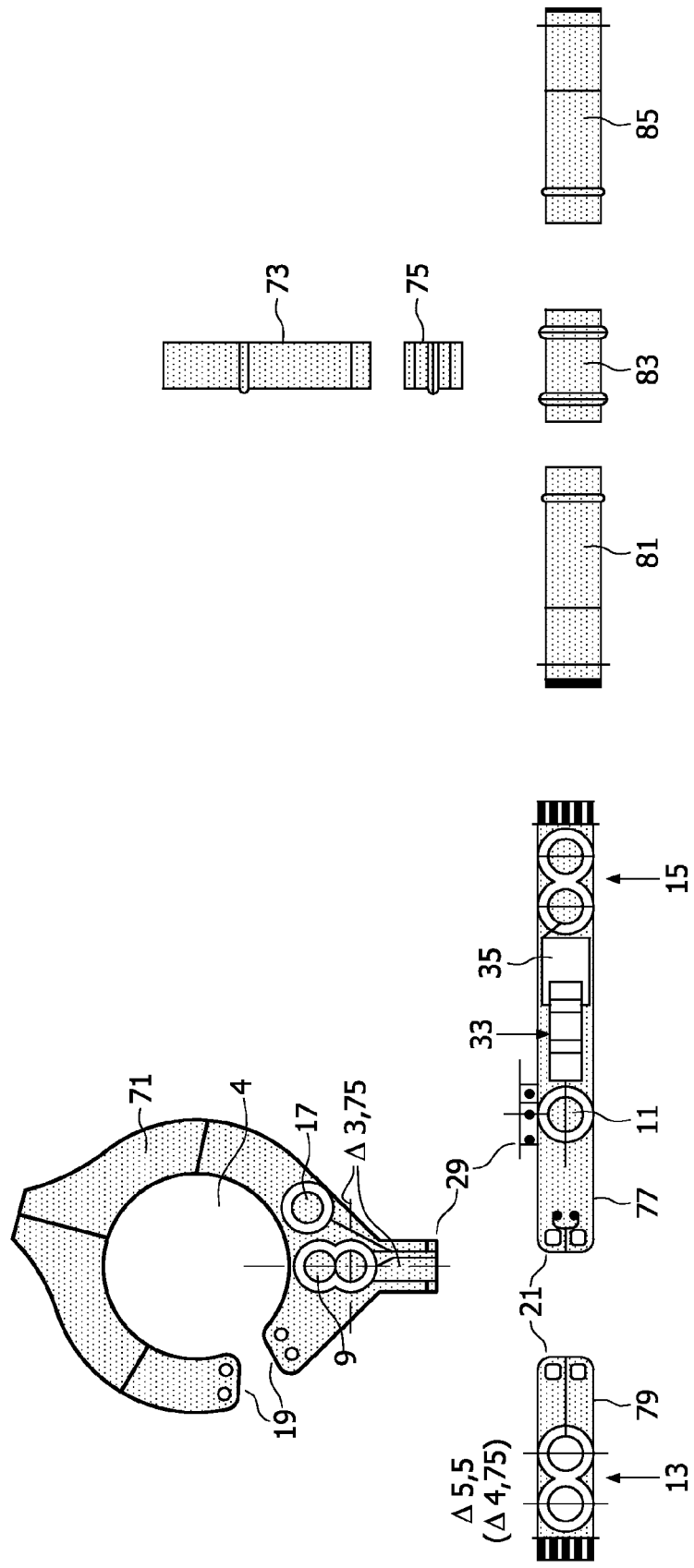
FIG. 2 shows the belt device of FIG. 1 by displaying the single portions.

Below, the belt system is described in principle on the basis of FIGS. 1 and 2. The belt device 1 comprises a collar portion 3 and a torso portion 5. The belt system 1 is used to arrange five sensors 7. In the described embodiment dry active rubber electrodes 7 are used. Dry rubber electrodes are comfortable to wear. Dry, active rubber electrodes are reusable, have a short set-up time and do not cause skin irritation. Further dry electrodes generate signals of high reliability.

In the shown embodiment a top sensor 9 is arranged in a short distance under the larynx. A sternum sensor 11 is arranged in a distance under the top sensor. By the design of the collar portion the skin contact of the top sensor is maintained. Especially the ring around the neck with none plane structure assists a good skin contact of the top sensor 9.

Further a left side sensor 15 and a right side sensor 13 are arranged on the height of the sternum sensor 11 on both sides of the upper body of the wearer. A ground sensor 17 is arranged on the height of top sensor 9. As described above this sensor positions are only a possible arrangement, which is dependent of the intended use of the belt system. The position of the ground sensor is more flexible as the position of the other sensors.

The collar portion 3 comprises an opening 4 for the neck and a first closure 19, which is arranged on the front side 23. This first closure is part of the portion of the collar portion, which surrounds the neck. Because of the position of the top sensor 9 and the sternum sensor 11 the first closure is arranged on the right or left side. The position can be adapted depending on whether the patient is right-handed or left-handed.

The top sensor 9 and the ground electrode 17 are arranged on the front side 23 too. The top sensor 9 is adjustable in respect to the collar portion 3 in a range of about 4 cm. By an adjustment the sensor position can be fitted to the wearer to be well placed for generating reliable measurements.

Further the collar portion 3 comprises a connection 29 and an adjustable connection 27 to connect the collar portion 3 to the torso portion 5. In the shown example the adjustable connection 27 is arranged on the backside 25. This adjustable connection is used to fit the collar portion 3 to the height of the upper part of the wearer. The adjustment has to be done only one time before the first usage of the belt device by one individual. In the adjustment process also the sensors positions are adjusted to the body of the wearer. Normally a professional will execute the adjustment. After the adjustment is done, the wearer could put on and off the belt device by opening/closing first closure element 19 and second closure element 21. Therefore the wearer needs no help by a third person. The wearer has not to pull the belt device over the head, which makes it more comfortable to put belt device 1 on or off.

The torso portion 5 also comprises sensors. The sternum sensor 11 and the right 13 and left side sensors 15 are arranged by the torso portion 5. The left side sensor and the right side sensor are adjustable 59 in a range of about 5 cm. An electronic module 33 is arranged by torso portion 5. The electronic module comprises a digital/analog converter, a storage module 67, a wireless link 69 and a small battery 35. The electronic module 35 could be split up in separate parts. All of the sensors are connected to the electronic module 33. Electronic connections 61 are integrated in the second closure element 21 and the connection 29.

The part 71 of the collar portion 3 is made of foamed material, which is very soft and comfortable to wear on the skin. On the backside 23 a part of the collar portion straps 73, 75 are arranged. The strips are used for adjustment. By the upper strap 73 the length is adjustable in a range of 6.5 cm. Elastic straps could be used.

The front part 79, 77 of the torso portion 5 is made of foamed material. The torso portion 5 also comprises straps 81, 83, 85, which are arranged on the backside 25. The length of the straps can be adjusted to adjust the torso portion 5 to the size of the user. The length of the straps 81 and 85 are each adjustable in a range of 9 cm. The length of the straps is adjusted in such a way that skin contact of the electrodes is assured. By the adjustment of the length of the straps the contact pressure of the sensors can be adjusted.

In some cases pressure elements are used to make sure that the sensor element has a good skin contact. Especially if the person is in motion there is a high risk that the skin contact of the sensors is interrupted. Especially if the sensor is arranged in a recess of the bumpy skin surface it is difficult to generate a high contact pressure to the sensor. In that case pressure elements 31 could be used to support the generation of a contact pressure.

Figure 3:
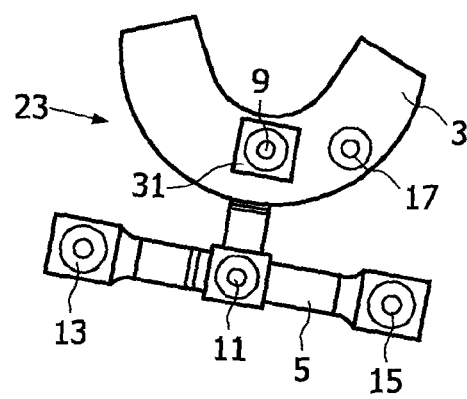
FIG. 3 shows a different design of the belt device in front view.
Figure 4:
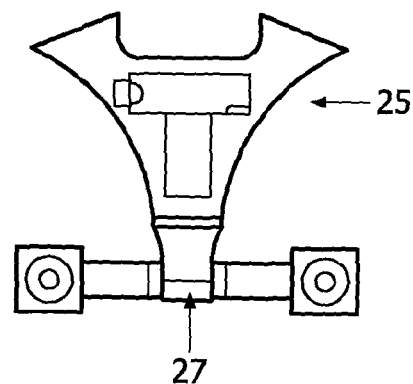
FIG. 4 shows the belt device of FIG. 2 in back view.

In FIGS. 3 and 4 an alternative design of the collar portion 3 is shown. In this embodiment the electronic module 33 is arranged on the backside of the collar portion 3. In some cases parts of the electronic module could be used as a pressure module, wherein that part of the electronic module is arranged on the sensor on the opposite side of the skin. By tightening the collar portion the sensor is pressed on the skin, wherein the module arranged on the sensor is pushed in direction of the skin.

Figure 5:
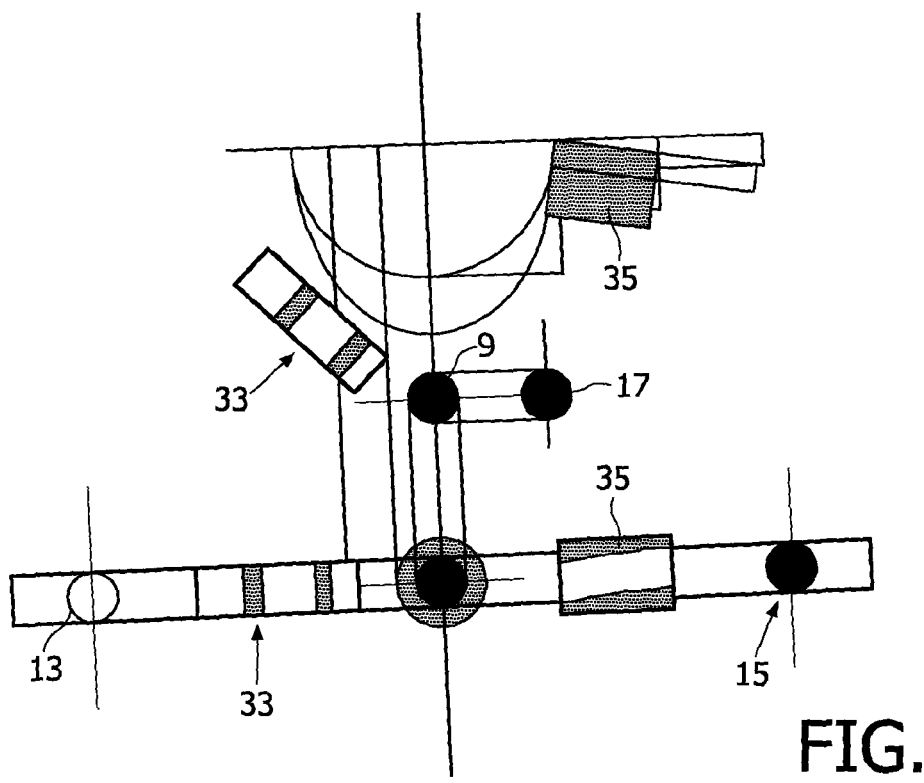
FIG. 5 shows schematically different possibilities of the arrangement of the battery and the electronic module.

In FIG. 5 different arrangements of the electronic module 33 are displayed. In this case the battery 35 is arranged separated from the electronic module 33.

To provide a belt device system a number of different sized collar portions 3 and a number of different sized torso portions 5 are provided. All of the collar portions 3 can be used in combination with each of the torso portions 5. Every collar portion 3 is assigned to a range of the height of the upper part of the body of the patient/wearer and every one of the torso portions 5 is assigned to a range of the thorax circumference size. In dependence of the size of the upper part of the wearer a torso portion 5 and a collar portion 3 is selected. Then the selected collar portion 3 is connected with the selected torso portion 5 by the connection 29 and the adjustable connection 27 to compose one possible belt device 1.

In table 2 the steps of different sized torso portions 5 and collar portions 3 are listed. In that case one collar is assigned to five established clothing sizes. So by this relatively small number of collar portions 3 and torso portions 5 a large range of people with different size are covered. In that case the collar portion 3 could be adjusted in a range of ca. 6.5 cm. One torso portion could be modified in a range of 19 cm. By making the range of adjustment smaller the belt device system could be fitted more precisely and the length of overlapping strips are reduced. Further by integrate more adjustment possibilities an adjustment could be done more precisely. The disadvantage is that then an adjustment becomes more complicate and higher prices are generated by the adjustable elements and adjustable connections. For a further reduction of the different sized collar portions and torso portions adapters could be used to avoid long surmounting straps in the case of the adjustment on the smallest position of the selected collar/torso portion.

Especially by interchange of connection 29 into a further adjustable connection it can make sure that the position of the neck is always placed in the middle of the opening 4 of the collar portion 3.

To adjust the belt system to a wearer, first the torso portion 5 is tighten up by the use of the adjustable straps 81, 85. Then the collar portion 3 is tightened up by the use of the adjustable connection.

Fastening devices such as Velcro and snap fastening can be used for fastening of electrodes, cables and electronics. So separate production of wearable and electronics part, easy assembly and disassembly is enabled.

In table 1 concrete sensor positions are listed. In that example a 39 old person was the wearer. His body height is 184 cm and his weight is 75 kg. The sharp perimeter is 39 cm and the chest perimeter is 95 cm. The waist perimeter is 86 cm. The height of the upper part of the body is about 50 cm. His established cloth size is 48 of the German cloth size. The height of the Sternum measured from the sharp is 30 cm. That location is the correct position for the sternum sensor 11. The chest perimeter is 93.5 cm at the height of the sensors held by the torso portion 5. These are the left side sensor 15, right side sensor 13 and the sternum sensor 11. The measured distance from lower side of the larynx down to sternum sensor position is 12.5 cm. The measured distance from the neck down to the top sensor 9 position is 17 cm. The distance between the top sensor 9 position and the sternum sensor 11 position is 7.5 cm.

In table 2 the established sizes are listed. Five established sizes are covered by one torso portion 5, which can be adjusted in a range of 15 cm.

LIST OF REFERENCE NUMBERS

| | |
|---|---|
| 1 | belt device |
| 3 | collar portion |
| 4 | opening (for the neck) |
| 5 | torso portion |
| 7 | sensor element |
| 9 | top sensor |
| 11 | sternum sensor |
| 13 | right side sensor |
| 15 | left side sensor |
| 17 | ground electrode/sensor |
| 19 | first closure element |
| 21 | second closure element |
| 23 | front side |
| 25 | back side |
| 27 | adjustable connection |
| 29 | connection |
| 31 | pressure element |
| 33 | electronic module |
| 35 | battery |
| 37 | transmitter |
| 39 | D/A converter |
| 41 | conductive closure element |
| 43 | data line |
| 45 | storage |
| 47 | dry sensor |
| 53 | foamed material |
| 55 | elastic belt |
| 59 | adjustment area of the sensors |
| 61 | electronic connection |
| 63 | length |
| 65 | sensor position |
| 67 | storage module |
| 69 | wireless link |
| 71 | collar |
| 73 | strap |
| 75 | strap |
| 77 | strap |
| 79 | strap |
| 81 | strap |
| 83 | strap |
| 85 | strap |

TABLE 1

| Point of measurement | Electrode/Sensor | |
|---|---|---|
| Body height | | 184 cm |
| Body weight | | 75 kg |
| Sharp perimeter | | 39 cm |
| Chest measurement | | 95 cm |
| Waist measurement | | 86 cm |
| Height of the upper part of the body | | Ca. 50 cm |
| size | | 48 (may be 98) |
| Height of sternum ex neck | Sternum sensor | 30 cm |
| Chest measurement at height of points of measurement | | 93.5 cm |
| Ca. ½ perimeter | Right side sensor + Left side sensor | 47.5 cm |
| Lower side of Larynx down to sternum | Top sensor | 12.5 cm |
| | Ground sensor | |
| Neck down to top sensor | | 17 cm |
| Top sensor to sternum sensor | | 7.5 cm |

TABLE 2

| Body height cm | Chest measurement cm | Waist measurement cm | Side length cm | size | No. | Maximum of difference of chest measurement |
|---|---|---|---|---|---|---|
| 160-164 | 78-81 | 66-96 | 96-99 | 40 | 1 | |
| 162-166 | 82-85 | 70-73 | 98-100 | 42 | 2 | |
| 164-168 | 84-87 | 72-75 | 99-101 | 43 | 3 | |
| 166-170 | 86-89 | 74-77 | 100-103 | 44 | 4 | |
| 168-173 | 90-93 | 78-81 | 102-104 | 46 | 5 | 15 cm |

TABLE 2-continued

| Body height cm | Chest measurement cm | Waist measurement cm | Side length cm | size | No. | Maximum of difference of chest measurement |
|---|---|---|---|---|---|---|
| 171-176 | 94-97 | 82-85 | 103-106 | 48 | 6 | |
| 174-179 | 98-101 | 86-89 | 105-108 | 50 | 7 | |
| 177-182 | 102-105 | 90-94 | 107-109 | 52 | 8 | |
| 180-184 | 106-109 | 95-99 | 108-110 | 54 | 9 | |
| 182-186 | 110-113 | 100-104 | 109-112 | 56 | 10 | 19 cm |
| 184-188 | 114-117 | 105-109 | 111-114 | 58 | 11 | |
| 185-189 | 118-121 | 110-114 | 112-115 | 60 | 12 | |
| 187-191 | 122-125 | 115-119 | 114-116 | 62 | 13 | |
| 189-193 | 126-129 | 120-124 | 115-117 | 64 | 14 | |
| 191-194 | 130-133 | 125-129 | 116-118 | 66 | 15 | 19 cm |
| | 134-137 | | | 68 | 16 | |
| | 138-141 | | | 70 | 17 | |
| | 142-145 | | | 72 | 18 | |
| | 146-149 | | | 74 | 19 | |
| | 150-153 | | | 76 | 20 | 19 cm |

The invention claimed is:

1. A belt device comprising;
a torso portion,
a collar portion connected to the torso portion by a first connection and a second connection,
sensor elements arranged at predetermined positions on the torso portion and the collar portion, and
at least a first closure element and a second closure element, wherein the first closure element is part of a front side of the collar portion and the second closure element is part of a front side of the torso portion,
wherein at least one of the first connection and the second connection is an adjustable connection element which allows a user to adjust a distance between the collar portion and the torso portion.

2. The belt device of claim 1, wherein the adjustable connection element is arranged at a backside of the belt device.

3. The belt device of claim 2, wherein the length of the torso portion is adjustable.

4. The belt device of claim 1, wherein the adjustable connection element enables a detachable connection of the collar portion and the torso portion.

5. The belt device of claim 1, comprising a pressure element to provide pressure to at least one of the sensor elements to guarantee continuous contact of a sensor element with the skin of the wearer.

6. The belt device of claim 5, wherein the pressure element is adjustable.

7. The belt device of claim 5 comprising an electronic module arranged on the torso portion.

8. The belt device of claim 7, wherein the electronic module is at least part of the pressure element.

9. The belt device of claim 7, wherein the second closure element comprises an electric connection for power and/or data transfer.

10. The belt device of claim 7, wherein the electronic module comprises a storage module to collect and store ECG data.

11. The belt device of claim 7, wherein the electronic module comprises a wireless link for data transfer.

12. The belt device of claim 1, wherein positions of the sensor elements are adjustable.

13. The belt system of claim 1, wherein parts of the torso portion and collar portion are made from foamed material.

14. The belt device of claim 1, wherein the belt device consists of five sensor elements arranged at predetermined positions which cannot be changed by the user.

15. A method to fit a belt device to a wearer comprising:
selecting a collar portion, which is sized with respect to an upper body part of the wearer,
selecting a torso portion which is sized with respect to a waist of the wearer,
connecting the selected torso portion with the selected collar portion via a first connection and a second connection,
adjusting a length of the collar portion,
adjusting the torso portion,
wherein the adjusting of the length of the collar portion and the adjusting of the torso portion aligns one or more of a plurality of sensors located on the collar portion and torso portion.

* * * * *